United States Patent
Steinle et al.

(10) Patent No.: US 11,494,984 B2
(45) Date of Patent: Nov. 8, 2022

(54) ATLAS-BASED CALCULATION OF A FLIGHT-PATH THROUGH A VIRTUAL REPRESENTATION OF ANATOMICAL STRUCTURES

(71) Applicant: Brainlab AG, Munich (DE)

(72) Inventors: Wolfgang Steinle, Munich (DE); Nils Frielinghaus, Heimstetten (DE); Dominik Fischer, Munich (DE); Christoffer Hamilton, Aschheim (DE)

(73) Assignee: Brainlab AG, Munich (DE)

( * ) Notice: Subject to any disclaimer, the term of this patent is extended or adjusted under 35 U.S.C. 154(b) by 264 days.

(21) Appl. No.: 16/083,309

(22) PCT Filed: Mar. 31, 2016

(86) PCT No.: PCT/EP2016/057005
§ 371 (c)(1),
(2) Date: Sep. 7, 2018

(87) PCT Pub. No.: WO2017/167365
PCT Pub. Date: Oct. 5, 2017

(65) Prior Publication Data
US 2019/0080513 A1    Mar. 14, 2019

(51) Int. Cl.
*G06T 19/00*    (2011.01)
*A61B 34/10*    (2016.01)
(Continued)

(52) U.S. Cl.
CPC ............ *G06T 19/003* (2013.01); *A61B 34/10* (2016.02); *G06F 16/9038* (2019.01);
(Continued)

(58) Field of Classification Search
CPC ........ A61B 2034/105; A61B 2034/107; A61B 34/10; G06F 16/9038; G06T 19/003; G06T 2207/20128; G06T 2210/41; G06T 7/0012
(Continued)

(56) References Cited

U.S. PATENT DOCUMENTS 6,083,170 A * 7/2000 Ben-Haim ........... A61B 5/0422
                                                                  600/462
6,496,188 B1    12/2002 Deschamps et al.
(Continued)

FOREIGN PATENT DOCUMENTS

DE    102005009271 A1    3/2004

OTHER PUBLICATIONS

Stephen Yip et al. "Development and evaluation of an articulated registration algorithm for human skeleton registration." Institute of Physics and Engineering in Medicine. vol. 59. Mar. 5, 2014.
(Continued)

*Primary Examiner* — Charles N Appiah
*Assistant Examiner* — Nicole M Louis-Fils
(74) *Attorney, Agent, or Firm* — Middleton Reutlinger

(57) ABSTRACT

The invention relates to a computer-implemented medical method for determining a virtual flight-path (1) with respect to a virtual representation (2) of at least one anatomical structure, the method comprising executing, on a processor of a computer, the steps of:—acquiring, on the processor, patient image data describing at least one patient image showing at least one anatomical structure of a patient; —acquiring, on the processor, atlas data describing at least one model of the at least one anatomical structure; —determining, by the processor and based on the patient image data and the atlas data, representation data describing a virtual representation of the at least one anatomical structure;
(Continued)

—acquiring, on the processor, requirement data describing at least one requirement for at least one flight-path (1); and—determining, by the processor and based on the representation data and the requirement data, flight-path data describing at least one virtual flight-path (1) with respect to the virtual representation (2) of the at least one anatomical structure.

12 Claims, 2 Drawing Sheets

(51) Int. Cl.
  *G06F 16/9038* (2019.01)
  *G06T 7/00* (2017.01)
(52) U.S. Cl.
  CPC ...... *G06T 7/0012* (2013.01); *A61B 2034/105* (2016.02); *A61B 2034/107* (2016.02); *G06T 2207/20128* (2013.01); *G06T 2210/41* (2013.01)
(58) Field of Classification Search
  USPC ........................................................ 382/128
  See application file for complete search history.

(56) References Cited

U.S. PATENT DOCUMENTS

| | | | |
|---|---|---|---|
| 7,167,180 B1* | 1/2007 | Shibolet | G06T 7/13 345/418 |
| 2002/0052875 A1* | 5/2002 | Smith | G06F 16/30 |
| 2004/0097805 A1* | 5/2004 | Verard | A61B 1/00071 600/428 |
| 2005/0197558 A1* | 9/2005 | Williams | G09B 23/285 600/407 |
| 2007/0182731 A1 | 8/2007 | Gundel | |
| 2009/0093712 A1* | 4/2009 | Busch | A61B 6/032 600/424 |
| 2010/0256558 A1* | 10/2010 | Olson | A61B 5/042 604/95.01 |
| 2012/0201433 A1* | 8/2012 | Iwasaki | A61B 1/00009 382/128 |
| 2015/0363937 A1 | 12/2015 | Weistrand | |
| 2016/0022286 A1* | 1/2016 | Borries | A61B 17/15 606/87 |
| 2016/0070436 A1* | 3/2016 | Thomas | A61B 6/032 715/771 |

OTHER PUBLICATIONS

International Search Report and Written Opinion issued in Application No. PCT/EP2016/057005 dated Dec. 19, 2016.

* cited by examiner

ATLAS-BASED CALCULATION OF A FLIGHT-PATH THROUGH A VIRTUAL REPRESENTATION OF ANATOMICAL STRUCTURES

The present invention relates to a computer-implemented method for determining a virtual flight-path with respect to a virtual representation of at least one anatomical structure, a corresponding computer program, a non-transitory storage medium storing such a program and a computer for executing the program, as well as a system for determining a virtual flight-path with respect to a virtual representation of at least one anatomical structure, comprising such a computer.

TECHNICAL BACKGROUND

Methods for planning paths for virtual endoscopy are known, for example from U.S. Pat. No. 6,496,188, wherein CT or MR volumetric images are used to visualize the inside of anatomical structures without the need to use a physical endoscope. Those methods operate on actual image data of a specific patient having a specific medical condition.

The present invention allows for a more convenient visualization of a flight-path through a virtual representation of anatomical structures, that is suitable for general training purposes as well as for the preparation of a procedure performed on a specific patient.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or combination of the features described in this section.

The disclosed method provides a virtual representation of anatomical structures, which is obtained by processing patient specific images together with corresponding data obtained from an anatomical atlas. Further, a flight-path fulfilling predefined requirements is calculated with respect to the virtual representation of the anatomical structures, so that data is obtained that describes the appearance of the anatomical structures when seen from along the calculated flight-path. This data may then be visualized on a display, giving the viewer the impression to fly along a desired flight-path with respect to the anatomical structures, particularly with respect to anatomical structures which are of special interest for the viewer, such as pathological structures or structures relevant to a medical or surgical procedure.

GENERAL DESCRIPTION OF THE PRESENT INVENTION

In this section, a description of the general features of the present invention is given, for example by referring to possible embodiment of the invention.

In general, the invention reaches the aforementioned object by providing, in a first aspect, a computer-implemented method for determining a virtual flight-path with respect to a virtual representation of at least one anatomical structure. The method comprises executing, on at least one processor of at least one computer, the following exemplary steps which are executed by the at least one processor.

In a (for example first) exemplary step, patient image data is acquired which describes (for example, defines) a digital image of a patient that shows at least one anatomical structure of a patient. This image may of course show anatomical structures of the patient which are of special interest.

In a further (for example second) exemplary step, atlas data is acquired which describes (for example, defines) at least one model of the at least one anatomical structure for which patient specific image data is acquired.

In a further (for example third) exemplary step, representation data is determined, which describes (for example, defines) a virtual representation of the at least one anatomical structure. This virtual representation is obtained by combining the patient specific image data and the general atlas data, for example by matching the patient image data to the anatomical atlas. This not only allows for the identification of organs and anatomical data in the patient's images, but also to classify and mark anatomical structures for visualization purposes. For example, anatomical structures such as organs, bones, vessels or pathological structures such as tumors may be marked and may be color coded.

In a further (for example fourth) exemplary step, requirement data is acquired describing at least one requirement for at least one flight-path. In other words, the framework for the preferably three-dimensional course of at least one flight-path with respect to one or more anatomical structures is defined. For example, the three-dimensional position of a starting point for the flight-path may be defined together with a plurality of waypoints to be passed by the flight-path, such that a later "flight" with respect to the virtual representation of the anatomical structures fulfills certain constraints, such as passing certain structures of interest while avoiding vessels or other sensitive anatomical structures. Further, the flight-path may pass through natural cavities but may also "cross" certain structures/organs in a desired manner. A large amount of constraints/requirements for the flight-paths are conceivable, an exemplary but not exhaustive list of which is discussed further below.

In a further (for example fifth) exemplary step, flight-path data is determined which describes at least one virtual flight-path with respect to the virtual representation of the at least one anatomical structure. In other words, the preferably three-dimensional course of at least one flight-path is calculated, which may also involve calculating the visual appearance of the virtual representation of the anatomical structures as seen from along the flight-path. Additionally, the course of the at least one flight-path is calculated to fulfill the given constraints defined beforehand.

As already indicated further above, the step of the inventive method for determining representation data may involve acquiring critical structure data describing at least one critical structure contained in the at least one anatomical structure. Such critical structures may be represented by pathological structures or any structures of interest which are desired to be seen and visually observed from along the flight-path. Consequently, the flight-path may pass the vicinity of at least one or a plurality of such critical structures. Further, a critical structure may be represented by a target the flight-path is supposed to end at. Such critical structures may be defined directly in the obtained image data of the patient, for example by a manual segmentation of the respective anatomical structures. One or more critical structures may however also be identified by registering the patient image data with the anatomical atlas that already contains information as to the critical structures to be identified, for example information as to the position, form and/or size of the critical structures. Additionally or alternatively, one or more critical structures may be defined later on, for example during a flight along an already calculated flight-path. For example, during a "flight" along the flight-path, a viewer may decide to have a closer look on structures which have not been identified as critical structures yet. After having identified the new critical structures to be observed, a re-calculation of the flight-path will be performed and the "flight" will continue along the new/amended flight-path.

Of course, it is conceivable that the virtual representation may contain any desired number of anatomical structures of the patient. For example, the virtual representation may contain only those anatomical structures which are of interest for preparing a certain procedure on the actual patient. On the other hand however, the virtual representation may be a "full" representation of a certain body part of a patient the flight-path is planned to cross through so as to provide a most realistic simulation for a later procedure.

Moreover, the flight-path, particularly the three-dimensional course of the flight-path may be defined in dependence on the at least one critical structure. While it is conceivable that the flight-path passes each of the defined critical structures at a predetermined distance, allowing a detailed observation of the critical structure, it may also be desirable that a viewer moving along the flight-path "circles" at least one of the defined critical structures, before moving on to a subsequent critical structure. Further, a critical structure may represent the end of the flight-path, i.e. the flight-path ends at a critical structure, particularly at a predetermined distance from the critical structure.

In addition to the at least one critical structure, one or more waypoints may be defined, which are to be passed by the flight-path.

It is also conceivable that the flight-path, particularly its starting point, is calculated as a function of a medical indication obtained for the actual patient. For example, the starting point for the flight-path may be set at the entrance of one nostril, wherein the medical indication may also affect the decision whether the left or the right nostril is chosen as a starting point.

In a further embodiment of the present invention, the step of determining flight-path data involves utilizing at least one path-finding algorithm for determining desirability of at least one flight-path and/or selecting a desirable flight-path, and in particular involves acquiring path-finding data describing at least one criterion for the flight-path, the at least one criterion being selected from the group consisting of:
  a cut-through criterion for at least one anatomical structure, describing whether the flight-path is to pass through or is to circumnavigate the respective anatomical structure;
  a move-to-side criterion for at least one anatomical structure, describing whether the flight-path is to continue unamended, with the respective anatomical structure moving out of the flight-path, or is to circumnavigate the respective anatomical structure;
  a path-index criterion for at least one anatomical structure and/or for at least one intermediate area between at least two anatomical structures, describing desirability for the flight-path to pass through the respective anatomical structure or the respective intermediate area;

and wherein the flight-path is defined in dependence on the at least one criterion.

In other words, a path-finding algorithm may be employed, that choses from a plurality of possible flight-paths the most desirable one, which may for example be a flight-path that crosses the fewest sensitive anatomical structures, or that provides the fastest/easiest access to a target of a planned procedure. Moreover, the algorithms may be utilized in conjunction with other requirements to find a desirable flight-path, for example between predefined waypoints and/or critical structures.

In order to choose the most desirable flight-path, one or more criteria may be considered. For example, a criteria may be defined for each of the anatomical structures the planned flight-path would pass through, wherein the criteria describes for each of those anatomical structures whether the flight-path may cut through the anatomical structure, or is not allowed to cut through the anatomical structure. The latter may be the case for any vessels and other sensitive structures that must not be harmed during a later procedure, for example by advancing an endoscopic instrument through this structure. Another criterion may define whether a corresponding anatomical structure may be displaced by an instrument being advanced along that flight-path during a later procedure, which may be the case for soft-tissue, or whether the anatomical structure cannot be displaced, which may be the case for any bony structures. Any other criteria can be defined in addition to or alternatively to the above described criteria, which may define a "desirability" for a flight-path to pass by or through anatomical structures or intermediate spaces between the anatomical structures.

According to a further embodiment, a flight-pass, particularly its starting point may be defined based on tracking data that is obtained from a medical tracking and/or navigation system. If a surgical procedure already takes place during the calculation of the flight path, the starting point may be set in accordance with the navigation system, i.e. the current position of an instrument may be defined as a starting point. This also includes starting points that are inside the patient's anatomy.

According to a further embodiment of the present invention and based on the representation data and the flight-path data, the virtual representation of the at least one anatomical structure and/or the at least one critical structure as seen by moving along the flight-path, is visualized on a medical display, wherein the visualization may provide at least one of the following features:
  at least one anatomical object can be cut away or rendered invisible depending on the medical indication and/or the current position along the flight-path;
  the viewer can switch between a plurality of flight-paths that may or may not reflect actual surgical pathways;
  at predetermined points of a flight-path from which more than one flight-path continue towards or with respect to the critical structure, or anywhere along a flight-path, indication-specific labels, arrows, measurements, recommendations for surgical instrument, color coding for critical structures, distance to target, expected surgery time to target, expected surgery time to end of procedure, warnings and/or other information related to anatomical structures and/or flight-paths can be indicated;
  the speed along the flight-path can be selected to be proportional to an indication-specific weighted average speed of a surgical procedure along that flight-path;
  at a predetermined or any chosen point of a flight-path, images and/or videos, particularly obtained from an endoscope, a microscope and/or other sources can be shown, particularly in a picture-in-picture-modality or as an overlay over the virtual representation;

at a point where the flight-path reaches or passes by a critical structure, or any other chosen point along the flight-path, an alternative, particularly circular flight-path around the critical structure can be chosen by the user;

a section of the flight-path of any length can be defined, particularly of a circular flight-path around a critical structure, for which the viewing direction extending from the flight-path is continuously directed towards the critical structure;

at any point of the flight-path, the orientation of the viewing direction with respect to the flight-path can be changed, particularly to at least one predefined value such as 0°, 30°, 45° or any other value, wherein the viewing direction can be in particular changed automatically, based, for example, on the indication data and the atlas data.

In a second aspect, the invention is directed to a system for determining a virtual flight-path with respect to a virtual representation of at least one anatomical structure. The system therefore comprises at least one computer having at least one processor that is adapted to perform a method as described above.

In a third aspect, the invention is directed to a computer program, which when running on at least one processor of at least one computer or when loaded into at least one memory of at least one computer, causes the at least one computer to perform an above-described method.

In a fourth aspect the invention is directed to a non-transitory computer-readable storage medium on which the program according to the third aspect is stored.

In a fifth aspect, the invention is directed to at least one computer, comprising at least one processor and at least one memory, wherein the above described program is running on the processor or is loaded into the memory or wherein the at least one computer comprises the above described program storage medium.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital light box. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

The invention also relates to a navigation system for computer-assisted surgery, comprising:

the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are for example vectors of a deformation field. These vectors are determined by the optimization algorithm in such a way as to result in an optimum degree of similarity. Thus, the optimum degree of similarity represents a condition, for example a constraint, for the optimization algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimizing problem is for example solved iteratively, for example by means of an optimization algorithm which is for example a first-order optimization algorithm, such as a gradient descent algorithm. Other examples of optimization algorithms include optimization algorithms which do not use derivations, such as the downhill simplex algorithm, or algorithms which use higher-order derivatives such as Newton-like algorithms. The optimization algorithm preferably performs a local optimization. If there is a plurality of local optima, global algorithms such as simulated annealing or generic algorithms can be used. In the case of linear optimization problems, the simplex method can for instance be used.

In the steps of the optimization algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighboring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

DESCRIPTION OF THE FIGURES

In the following, the invention is described with reference to the appendant Figures which represent a specific embodiment of the invention. The scope of the invention is however not limited to the specific features disclosed in the context of the Figures.

FIG. 1 shows a two-dimensional representation 2 of a patient's head, through which a flight-path 1 is guided. Starting at starting point 5, the flight-path 1 passes three waypoints 4 and ends at target point which is represented by a critical structure 3, a later medical procedure is planned to be performed on.

FIG. 2 shows another situation, with flight-path 1 being directed through a three-dimensional representation 2 to a target 3.

Even though FIGS. 1 and 2 show the virtual representation 2 together with the flight-path 1 from a distance, the virtual representation 2 may be shown and displayed to a viewer from along the flight-path 1, i.e. as if the viewer moves along the flight-path 1 through the virtual representation 2 of the anatomical structures.

Figure 1:
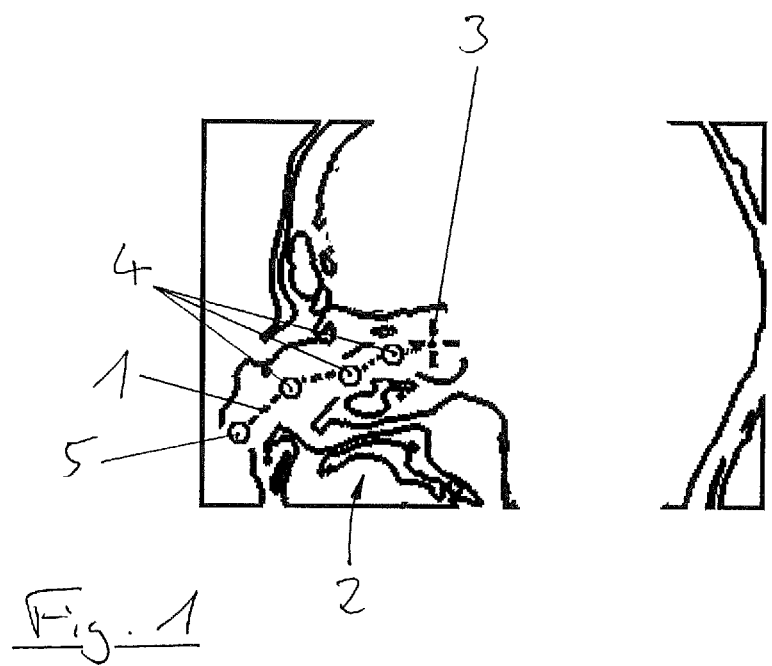
FIG. 1 shows a two-dimensional representation of a patient's head through which a flight-path is directed.
Figure 2:
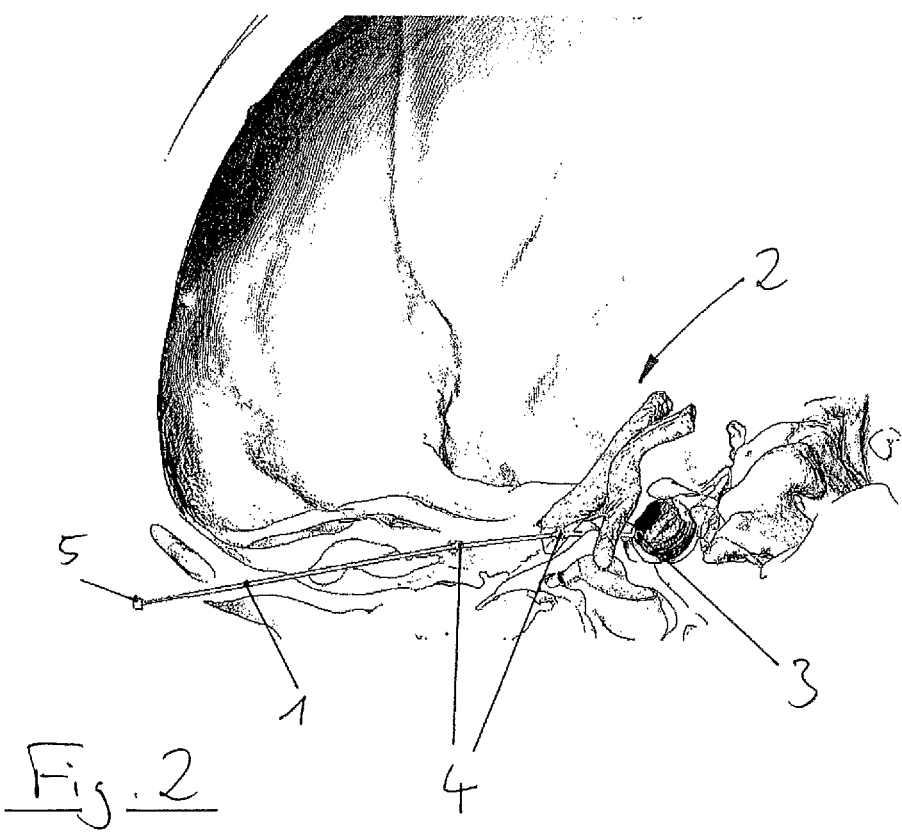
FIG. 2 shows a three-dimensional representation of a patient's head through which a flight-path is directed.

In the following, two specific embodiments for performing the inventive method are described, without limiting the invention to the specific features disclosed therein.

A specific procedure I may comprise the following steps:
1. Medical imaging of the patient is performed, e.g. CT, MR, PET and/or other medical imaging procedure so as to obtain patient image data.
2. The medical images are matched to an anatomical atlas that already contains information on flight-path criteria.
3. A medical professional executes the computer program, enters the patient's clinical/medical indication and defines one or more areas 3, 5 that shall be the goal of the visualized fly-through, for example observed during the fly-through.
4. The medical image data, atlas data and clinical indication data are combined to create one or more possible flight-paths 1 the user can choose.
5. The medical professional follows the calculated flight-path 1 in a visualization software and enhances his anatomical understanding of the patient and the critical structures 3.

A specific procedure II may comprise the following steps:
1. Medical imaging of the patient is performed, e.g. CT, MR, PET and/or other medical imaging procedure so as to obtain patient image data.
2. The medical images are matched to an anatomical atlas that already contains information on flight-path criteria.
3. A medical professional executes the computer program, enters the patient's clinical indication and defines one or more areas 3, 4, 5 that shall be the goal of the visualized fly-through, for example observe during the fly through.
4. The medical image data, atlas data and clinical indication data are combined to create one or more possible flight-paths the user can choose, comprising waypoints 4.
5. The medical professional selects a path 1 in a visualization software.
6. The medical professional may remove one or more waypoints 4 and add other waypoint 4.
7. The medical professional follows the calculated flight-path in a visualization software. At the waypoints 4, he uses mouse interaction to move around the visualization and look in different directions.
8. Later, during surgery, the medical professional updates the start point 5 of the flight-path 1 using a surgical navigation system, potentially combined with intra-operative imaging.

The invention claimed is:

1. A computer-implemented method for determining a virtual flight-path with respect to a virtual representation of at least one anatomical structure, the method comprising executing, on at least one processor of a computer, the steps of:
   acquiring, by the at least one processor, patient image data describing a three-dimensional patient image dataset showing at least one anatomical structure of a patient, wherein the patient image data is stored in a database;
   acquiring, by the at least one processor, atlas data describing at least one model of the at least one anatomical structure;
   determining, by the at least one processor and based on the patient image data retrieved from the database and the atlas data, representation data describing a three-dimensional virtual representation of the at least one anatomical structure;
   acquiring, by the at least one processor, requirement data describing at least one requirement for at least one flight-path; and
   determining, by the at least one processor and based on the representation data and the requirement data, flight-path data describing a three-dimensional course of at least one virtual flight-path with respect to the three-dimensional virtual representation of the at least one anatomical structure, wherein determining the flight-path data involves, utilizing at least one path-finding algorithm for determining desirability of the at least one flight-path and/or selecting a desirable flight-path, and involves acquiring path-finding data, based on a plurality of pre-defined criterions, for the at least one anatomical structure, and wherein each of the plurality of pre-defined criterions is stored in the database and the plurality of pre-defined criterions comprises:
      a cut-through criterion for the at least one anatomical structure, describing whether a flight-path is to pass through the respective anatomical structure or is to circumnavigate the respective anatomical structure, and
      a move-to-side criterion for the at least one anatomical structure, describing whether the flight-path is to continue unamended, with the respective anatomical structure moving out of the flight-path, or is to circumnavigate the respective anatomical structure, and
      a path-index criterion for the at least one anatomical structure and/or for at least one intermediate area between at least two anatomical structures, describing desirability for the flight-path to pass through the respective anatomical structure or through the respective intermediate area;
   wherein the flight-path is defined in dependence on at least one of the plurality of pre-defined criterions retrieved from the database, and;
   wherein the flight-path data describing the at least one virtual flight-path represents a visualization presented from a point passing along the at least one virtual flight-path.

2. The method of claim 1, wherein determining representation data involves acquiring critical structure data describing at least one critical structure contained in the at least one anatomical structure.

3. The method of claim 2, wherein the at least one critical structure includes at least one pathological structure of the patient.

4. The method of claim 2, wherein acquiring critical structure data involves defining the at least one critical structure within the three-dimensional patient image dataset and/or within the three-dimensional virtual representation.

5. The method of claim 1, wherein the atlas data describes at least one further anatomical structure.

6. The method of claim 2, wherein determining flight-path data involves defining the flight-path in dependence on the at least one critical structure.

7. The method of claim 1, wherein determining flight-path data involves acquiring waypoint data describing at least one waypoint that is to be passed by the flight-path, and wherein the flight-path data is also based on the waypoint data.

8. The method of claim 1, wherein determining flight-path data involves acquiring indication data describing at least one medical indication of the patient, and wherein a starting point of the flight-path is defined in dependence on the at least one medical indication.

9. The method of claim 1, wherein determining flight-path data involves acquiring a position of at least one point of the flight-path from tracking data obtained from a medical tracking system.

10. The method of claim 2 wherein, based on the representation data and the flight-path data, the three-dimensional virtual representation of the at least one anatomical structure and/or the at least one critical structure as seen by moving along the flight-path, is provided in output to a medical display, wherein the output provides at least one of the following features:
   at least one anatomical object is cut away or rendered invisible depending on the at least one medical indication and/or the current position along the flight-path;
   the provided output is operable to switch between a plurality of flight-paths that may or may not reflect actual surgical pathways;
   at predetermined points of the flight-path from which more than one flight-path continue towards or with respect to the at least one critical structure, or anywhere along the flight-path, indication-specific labels, arrows, measurements, recommendations for surgical instrument, color coding for critical structures, distance to target, expected surgery time to target, expected surgery time to end of procedure, warnings and/or other information related to anatomical structures and/or flight-paths are indicated;
   a speed along the flight-path is selected to be proportional to an indication-specific weighted average speed of a surgical procedure along that flight-path;
   at a predetermined or any chosen point of the flight-path, images and/or videos are shown;
   at a point where the flight-path reaches or passes by a critical structure, or any other chosen point along the flight-path, a circular flight-path around the critical structure is provided in the output;
   a section of the flight-path of any length is defined, particularly of the circular flight-path around the critical structure, for which a viewing direction extending from the flight-path is continuously directed towards the critical structure;
   at any point of the flight-path, the orientation of the viewing direction with respect to the flight-path is changed, wherein the viewing direction is changed in the provided output.

11. A system for determining a virtual flight-path with respect to a virtual representation of at least one anatomical structure, the system comprising:
   a computer having at least one processor and associated memory, the memory having instructions stored thereon that, when executed, perform the steps of:
   acquiring, by the at least one processor, patient image data describing a three-dimensional patient image dataset showing at least one anatomical structure of a patient wherein the patient image data is stored in a database;
   acquiring, by the at least one processor, atlas data describing at least one model of the at least one anatomical structure;
   determining, by the at least one processor and based on the patient image data retrieved from the database and the atlas data, representation data describing a three-dimensional virtual representation of the at least one anatomical structure;
   acquiring, by the at least one processor, requirement data describing at least one requirement for at least one flight-path; and
   determining, by the at least one processor and based on the representation data and the requirement data, flight-path data describing at least one virtual flight-path with respect to the three-dimensional virtual representation of the at least one anatomical structure, wherein determining the flight-path data involves utilizing at least one path-finding algorithm for determining desirability of the at least one flight-path and/or selecting a desirable flight-path, and involves acquiring path-finding data, based on a plurality of pre-defined criterions, for the at least one anatomical structure, and wherein each of the plurality of pre-defined criterions is stored in the database and the plurality of pre-defined criterions comprises:
      a cut-through criterion for the at least one anatomical structure, describing whether a flight-path is to pass through the respective anatomical structure or is to circumnavigate the respective anatomical structure, and
      a move-to-side criterion for the at least one anatomical structure, describing whether the flight-path is to continue unamended, with the respective anatomical structure moving out of the flight-path, or is to circumnavigate the respective anatomical structure, and
      a path-index criterion for the at least one anatomical structure and/or for at least one intermediate area between at least two anatomical structures, describing desirability for the flight-path to pass through the respective anatomical structure or through the respective intermediate area;
   wherein the flight-path is defined in dependence on at least one of the plurality of pre-defined criterions retrieved from the database, and;
   wherein the flight-path data describing the at least one virtual flight-path represents a visualization presented from a point passing along the at least one virtual flight-path.

12. A non-transitory computer-readable storage medium storing a computer program which, when executed on at least one processor of at least one computer, causes the at least one computer to perform the steps comprising:
   acquiring, by the at least one processor, patient image data describing a three-dimensional patient image dataset showing at least one anatomical structure of a patient wherein the patient image data is stored in a database;

acquiring, by the at least one processor, atlas data describing at least one model of the at least one anatomical structure;

determining, by the at least one processor and based on the patient image data and the atlas data, representation data describing a three-dimensional virtual representation of the at least one anatomical structure;

acquiring, by the at least one processor, requirement data describing at least one requirement for at least one flight-path; and determining, by the at least one processor and based on the representation data and the requirement data, flight-path data describing at least one virtual flight-path with respect to the three-dimensional virtual representation of the at least one anatomical structure, wherein determining the flight-path data involves utilizing at least one path-finding algorithm for determining desirability of the at least one flight-path and/or selecting a desirable flight-path, and involves acquiring path-finding data, based on a plurality of pre-defined criterions, for the at least one anatomical structure, wherein each of the plurality of pre-defined criterions is stored in the database and the plurality of pre-defined criterions comprises:

a cut-through criterion for the at least one anatomical structure, describing whether a flight-path is to pass through or is to circumnavigate the respective anatomical structure, a move-to-side criterion for the at least one anatomical structure, describing whether the flight-path is to continue unamended, with the respective anatomical structure moving out of the flight-path, or is to circumnavigate the respective anatomical structure, and a path-index criterion for the at least one anatomical structure and/or for at least one intermediate area between at least two anatomical structures, describing desirability for the flight-path to pass through the respective anatomical structure or through the respective intermediate area;

wherein the flight-path is defined in dependence on at least one of the plurality of pre-defined criterions retrieved from the database, and;

wherein the flight-path data describing the at least one virtual flight-path represents a visualization presented from a point passing along the at least one virtual flight-path.

* * * * *